(12) United States Patent
Peters et al.

(10) Patent No.: US 7,223,753 B2
(45) Date of Patent: May 29, 2007

(54) DIAZABICYCLIC BIARYL DERIVATIVES

(75) Inventors: Dan Peters, Malmoe (SE); Gunnar M. Olsen, Smoerum (DK); Elsebet Oestergaard Nielsen, Koebenhavn K (DK); Tino Dyhring Joergensen, Solroed Strand (DK); Philip K. Ahring, Bagsvaerd (DK)

(73) Assignee: Neurosearch A/S, Ballerup (DK)

( * ) Notice: Subject to any disclaimer, the term of this patent is extended or adjusted under 35 U.S.C. 154(b) by 458 days.

(21) Appl. No.: 10/703,556

(22) Filed: Nov. 10, 2003

(65) Prior Publication Data

US 2004/0127491 A1    Jul. 1, 2004

Related U.S. Application Data

(60) Provisional application No. 60/426,387, filed on Nov. 15, 2002.

(30) Foreign Application Priority Data

Nov. 11, 2002   (DK) .................... PA 2002 01737

(51) Int. Cl.
*A61P 25/00*   (2006.01)
*A61K 31/551*   (2006.01)
*A61K 31/495*   (2006.01)
*C07D 471/00*   (2006.01)
*C07D 243/00*   (2006.01)

(52) U.S. Cl. .................. 514/221; 514/249; 540/472; 540/556; 544/349

(58) Field of Classification Search ............... 514/221, 514/249; 540/472, 556; 544/349
See application file for complete search history.

(56) References Cited

U.S. PATENT DOCUMENTS

6,407,095 B1 *   6/2002   Lochead et al. ............ 514/221
2004/0106603 A1 *   6/2004   Coe et al. .................. 514/221

FOREIGN PATENT DOCUMENTS

| DE | 101 62 442 A1 | 7/2003 |
| EP | 1 219 622 A2 | 7/2002 |
| WO | WO 00/34279 A1 | 6/2000 |
| WO | WO 01/92259 A1 | 12/2001 |
| WO | WO 01/92260 A1 | 12/2001 |
| WO | WO 01/92261 A1 | 12/2001 |
| WO | WO 03/044019 A1 | 5/2003 |
| WO | WO 03/044020 A1 | 5/2003 |
| WO | WO 03/044024 A1 | 5/2003 |
| WO | WO 2004/029053 A1 | 4/2004 |

* cited by examiner

*Primary Examiner*—Brenda Coleman
(74) *Attorney, Agent, or Firm*—Birch, Stewart, Kolasch & Birch, LLP

(57) ABSTRACT

This invention relates to novel diazabicyclic biaryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

4 Claims, No Drawings

DIAZABICYCLIC BIARYL DERIVATIVES

This Nonprovisional application claims priority under 35 U.S.C. § 119(e) to U.S. Provisional Application Ser. No. 60/426,387 filed on Nov. 15, 2002, the entire contents of which are hereby incorporated by reference.

TECHNICAL FIELD

This invention relates to novel diazabicyclic biaryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

WO 00/34279, WO 01/92259, WO 01/92260, WO 01/92261, WO 03/044019, WO 03/044020, WO 03/044024 (Sanofi-Synthelabo), and DE 10162442 (Bayer AG) describe 1,4-diazabicyclo[3.3.2]nonane derivatives having affinity for nicotinic receptors.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diazabicyclic biaryl derivatives represented by Formula I

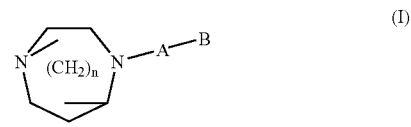

any of its enantiomers or any mixture of its enantiomers, or a pharmaceutically acceptable salt thereof, wherein n is 1, 2 or 3; and 'A" represents a bivalent phenyl group of the formula

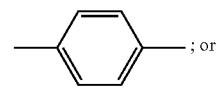

'A" represents a bivalent 5-membered aromatic monocyclic heterocyclic group selected from

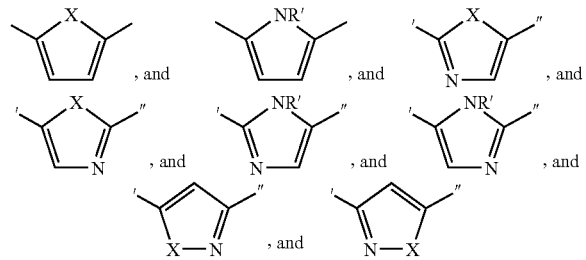

(read in the direction represented by ' and ");

wherein X represents O, S or Se; and R' represents hydrogen or alkyl; or

'A" represents a bivalent 6-membered aromatic monocyclic carbocyclic or heterocyclic group selected from

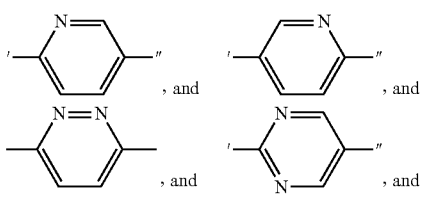

-continued

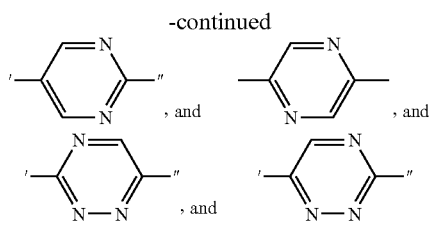

(read in the direction represented by ' and "); and

B represents an aromatic monocyclic or bicyclic carbocyclic group; or

B represents a 5–6 membered aromatic monocyclic heterocyclic group; or

B represents an aromatic bicyclic heterocyclic group;

which monocyclic or bicyclic, carbocyclic or heterocyclic groups may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR"', and —NR"SO2R"', wherein R" and R"', independently of one another represents hydrogen, alkyl, cycloalkyl, cycloalkyl-alkyl or phenyl; and a group of formula —CONR"R"' and —SO$_2$NR"R"', wherein R" and R"', independently of one another represents hydrogen, alkyl, cycloalkyl, cycloalkyl-alkyl or phenyl, or wherein R" and R"', together with the N-atom to which they are bound, form a heterocyclic ring;

provided however, if A represents an isoxazol-3,5-diyl, a thiazol-2,5-diyl, a 1,2,4-oxadiazol-3,5-diyl, a 1,3,4-oxadiazol-2,5-diyl, a 1,3,4-thiadiazol-2,5-diyl, pyridin-2,5-diyl, or a pyridazin-3,6-diyl group, then B is not a phenyl or substituted phenyl group; or if A represents a 1,2,4-oxadiazol-3,5-diyl group, then B is not a substituted or non-substituted thienyl, furanyl, pyridinyl, or benzothienyl group.

In its second aspect the invention provides pharmaceutical compositions comprising a therapeutically effective amount of the diazabicyclic biaryl derivative of the invention, or a pharmaceutically-acceptable addition salt thereof, together with at least one pharmaceutically-acceptable carrier or diluent.

In a further aspect the invention relates to the use of the diazabicyclic biaryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicyclic biaryl derivative of the invention.

Other objects of the invention will be apparent to the person skilled in the art from the following detailed description and examples.

DETAILED DISCLOSURE OF THE INVENTION

Diazabicyclic Biaryl Derivative

In a first aspect novel diazabicyclic biaryl derivatives are provided. The diazabicyclic biaryl derivatives of the invention may be represented by the general Formula I

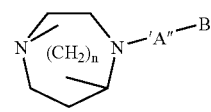

(I)

any of its enantiomers or any mixture of its enantiomers, or a pharmaceutically acceptable salt thereof, wherein n is 1, 2 or 3; and 'A" represents a bivalent phenyl group of the formula

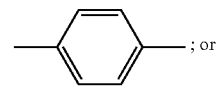

; or

'A" represents a bivalent 5-membered aromatic monocyclic heterocyclic group selected from

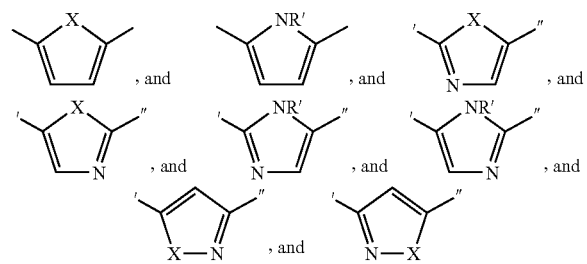

(read in the direction represented by ' and ");

wherein X represents O, S or Se; and R' represents hydrogen or alkyl; or

'A" represents a bivalent 6-membered aromatic monocyclic carbocyclic or heterocyclic group selected from

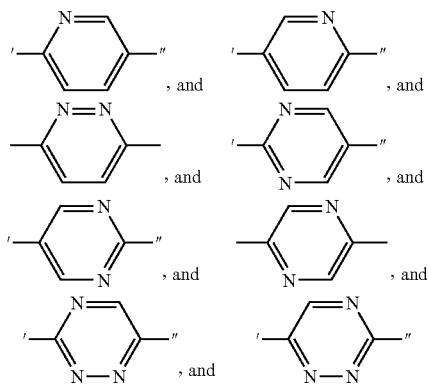

and (read in the direction represented by ' and "); and

B represents an aromatic monocyclic or bicyclic carbocyclic group; or

B represents a 5–6 membered aromatic monocyclic heterocyclic group; or

B represents an aromatic bicyclic heterocyclic group;

which monocyclic or bicyclic, carbocyclic or heterocyclic groups may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO2R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring;

provided however, if A represents an isoxazol-3,5-diyl, a thiazol-2,5-diyl, a 1,2,4-oxadiazol-3,5-diyl, a 1,3,4-oxadiazol-2,5-diyl, a 1,3,4-thiadiazol-2,5-diyl, pyridin-2,5-diyl, or a pyridazin-3,6-diyl group, then B is not a phenyl or substituted phenyl group; or if A represents a 1,2,4-oxadiazol-3,5-diyl group, then B is not a substituted or non-substituted thienyl, furanyl, pyridinyl, or benzothienyl group.

In a preferred embodiment the diazabicyclic biaryl derivative of the invention is a compound of Formula II

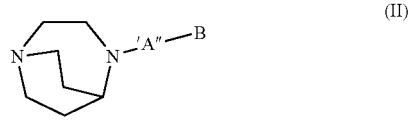

(II)

wherein 'A" and B are as defined above.

In another preferred embodiment the diazabicyclic biaryl derivative of the invention is a compound of Formula I or Formula II, wherein 'A" is as defined above and B represents an aromatic monocyclic or bicyclic carbocyclic group, which aromatic group may optionally be substituted one or more times with substituents selected from the group consisting of alkyl, cycloalkyl, cycloalkyl-alkyl, alkoxy, cyanoalkyl, halogen, $CF_3$, $OCF_3$, CN, amino and nitro; or B represents a 5–6 membered aromatic monocyclic heterocyclic group, which aromatic group may optionally be substituted one or more times with substituents selected from the group consisting of alkyl, cycloalkyl, cycloalkyl-alkyl, alkoxy, cyanoalkyl, halogen, $CF_3$, $OCF_3$, CN, amino and nitro; or B represents an aromatic bicyclic heterocyclic group, which bicyclic heterocyclic group may optionally be substituted one or more times with substituents selected from the group consisting of alkyl, cycloalkyl, cycloalkyl-alkyl, alkoxy, cyanoalkyl, halogen, $CF_3$, $OCF_3$, CN, amino and nitro.

In a more preferred embodiment the diazabicyclic biaryl derivative of the invention is a compound of Formula II wherein 'A" is as defined above; and B represents a 5–6 membered aromatic monocyclic heterocyclic group; or B represents an aromatic bicyclic heterocyclic group;

which monocyclic or bicyclic heterocyclic groups may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring.

In another preferred embodiment the diazabicyclic biaryl derivative of the invention is a compound of Formula I or Formula II, wherein B represents a phenyl or naphthyl group, optionally substituted one or more times with substituents selected from the group consisting of alkyl, cycloalkyl, cycloalkyl-alkyl, alkoxy, cyanoalkyl, halogen, $CF_3$, $OCF_3$, CN, amino and nitro.

In a third preferred embodiment the diazabicyclic biaryl derivative of the invention is a compound of Formula II wherein 'A" represents a 5-membered aromatic monocyclic heterocyclic group selected from

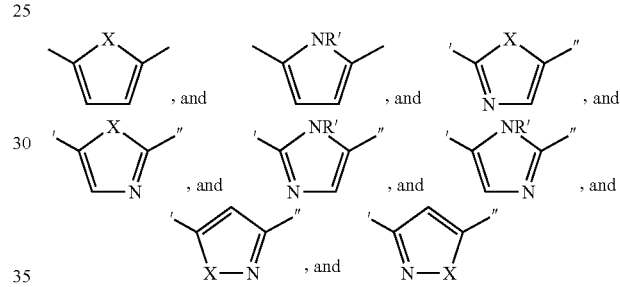

(read in the direction represented by ' and ");

wherein X represents O, S or Se; and R' represents hydrogen or alkyl; and

B represents an aromatic monocyclic or bicyclic carbocyclic group, which monocyclic or bicyclic carbocyclic groups may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring.

In a more preferred embodiment

'A" represents a 5-membered aromatic monocyclic heterocyclic group selected from

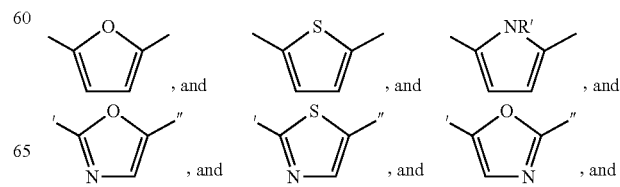

-continued

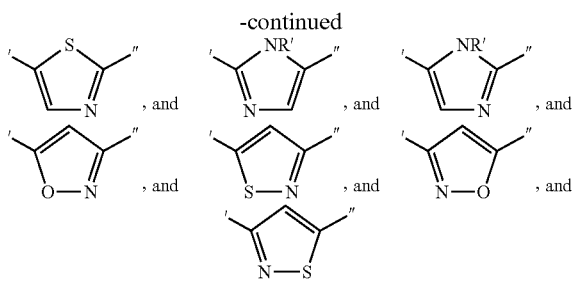

(read in the direction stated),
wherein R' represents hydrogen or methyl; and

B represents a phenyl or naphthyl group, which aromatic group may optionally be substituted one or two times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a piperidine, a piperazine, a morpholine or a thiomorpholine ring.

In an even more preferred embodiment
'A" represents a 5-membered aromatic monocyclic heterocyclic group selected from

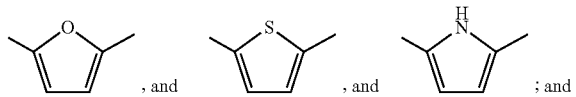

B represents a phenyl or naphthyl group, which aromatic group may optionally be substituted one or two times with substituents selected from the group consisting of alkyl, alkoxy, halo, $CF_3$, $OCF_3$, CN and nitro; and a group for formula —NR"COR'", and —NR"SO$_2$R'", wherein R" and R'", independently of one another represents hydrogen, alkyl or phenyl; and a group of formula —CONR"R'" and —SO$_2$NR"R'", wherein R" and R'", independently of one another represents hydrogen, alkyl or phenyl, or wherein R" and R'", together with the N-atom to which they are bound, form a piperidine, a piperazine, a morpholine or a thiomorpholine ring.

In a fourth preferred embodiment the diazabicyclic biaryl derivative of the invention is a compound of Formula I or Formula II wherein
'A" represents a bivalent phenyl group of the formula

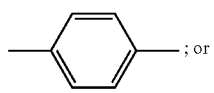; or or
'A" represents a 6-membered aromatic monocyclic carbocyclic or heterocyclic group selected from

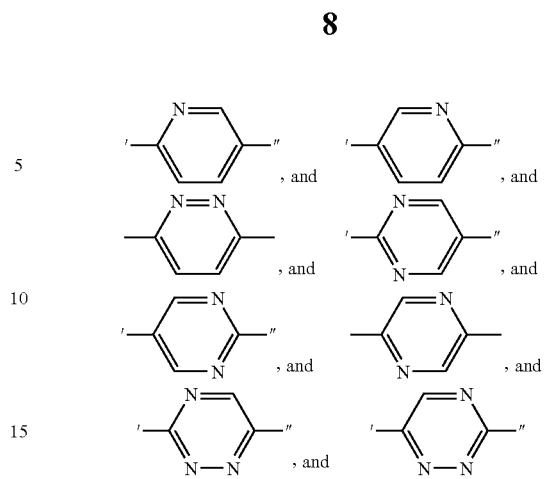

(read in the direction represented by ' and "); and
B represents an aromatic monocyclic or bicyclic carbocyclic group; or
B represents a 5–6 membered aromatic monocyclic heterocyclic group; or
B represents an aromatic bicyclic heterocyclic group;
which monocyclic or bicyclic, carbocyclic or heterocyclic groups may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring.

In a more preferred embodiment 'A" represents a bivalent phenyl group of the formula

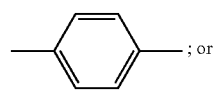; or or
'A" represents a 6-membered aromatic monocyclic carbocyclic or heterocyclic group selected from

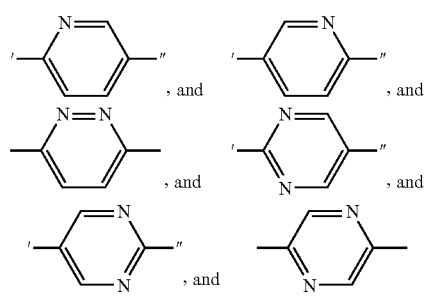

(read in the direction stated); and
B represents a phenyl or naphthyl group; or

B represents a 5-membered aromatic monocyclic heterocyclic group selected from

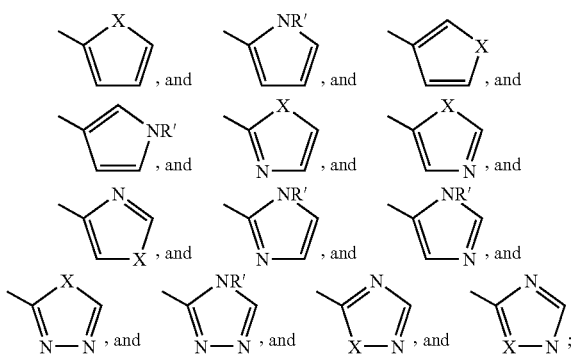

wherein X represents O, S or Se; and R' represents hydrogen or alkyl; or

B represents a 6-membered aromatic monocyclic heterocyclic group selected from

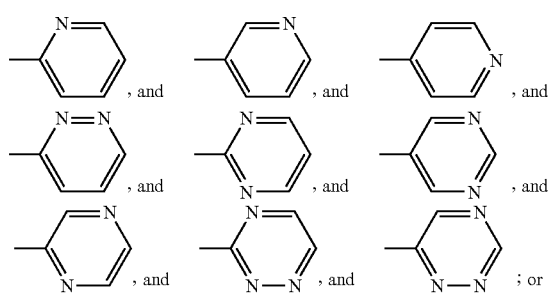

B represents an indolyl group;

which phenyl or naphthyl groups, or 5–6-membered monocyclic heterocyclic groups, or indolyl group may optionally be substituted one or more times with substituents selected from the group consisting of alkyl, cycloalkyl, cycloalkyl-alkyl, alkoxy, cyanoalkyl, halo, $CF_3$, $OCF_3$, CN, amino and nitro; and a group for formula —NR"COR'", and —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring; or which phenyl or naphthyl groups, or 5–6-membered monocyclic heterocyclic groups, or indolyl group may optionally be substituted one or more times with substituents selected from the group consisting of alkyl, cycloalkyl, cycloalkyl-alkyl, alkoxy, cyanoalkyl, halogen, $CF_3$, $OCF_3$, CN, amino and nitro.

In an even more preferred embodiment

'A" represents a bivalent phenyl group of the formula

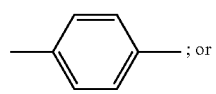 ; or

'A" represents a bivalent 6-membered aromatic monocyclic carbocyclic or heterocyclic group selected from

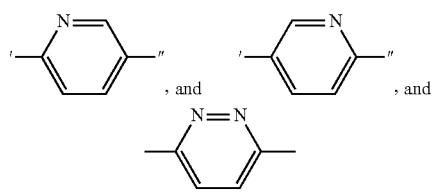

(read in the direction stated); and

B represents a phenyl group; or

B represents a 5-membered aromatic monocyclic heterocyclic group selected from

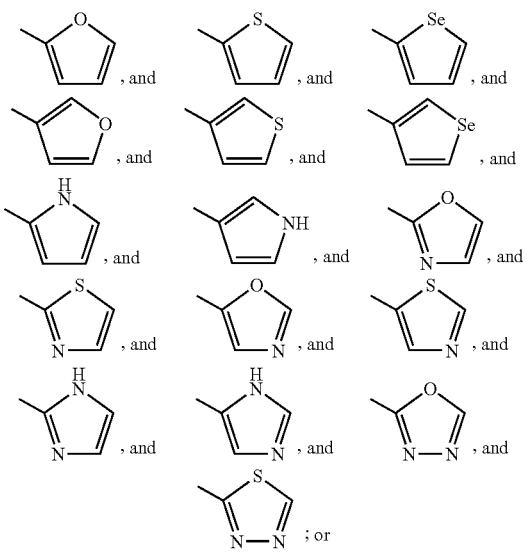

B represents a 6-membered aromatic monocyclic heterocyclic group selected from

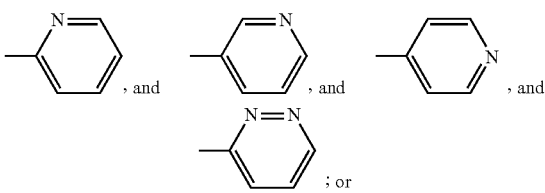

B represents an indol-2-yl, an indol-3-yl, an indol-5-yl or an indol-6-yl group;

which phenyl group, or 5–6-membered monocyclic heterocyclic groups, or indolyl groups may optionally be substituted one or more times with substituents selected from the group consisting of alkyl, alkoxy, halo, $CF_3$, $OCF_3$, CN and nitro; and a group for formula —NR"COR'", and —NR"SO$_2$R'", wherein R" and R'", independently of one another represents hydrogen, alkyl or phenyl; and a group of formula —CONR"R'" and —SO$_2$NR"R'", wherein R" and R'", independently of one another represents hydrogen, alkyl or phenyl, or wherein R" and R'", together with the N-atom to which they are bound, form a a piperidine, a piperazine, a morpholine or a thiomorpholine ring.

In a still more preferred embodiment 'A" represents a bivalent phenyl group of the formula

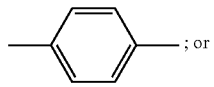

or

'A" represents a bivalent 6-membered aromatic monocyclic carbocyclic or heterocyclic group selected from

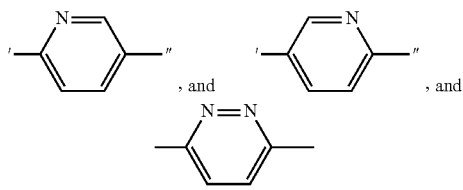

(read in the direction stated); and

B represents a phenyl group; or

B represents a 5-membered aromatic monocyclic heterocyclic group selected from

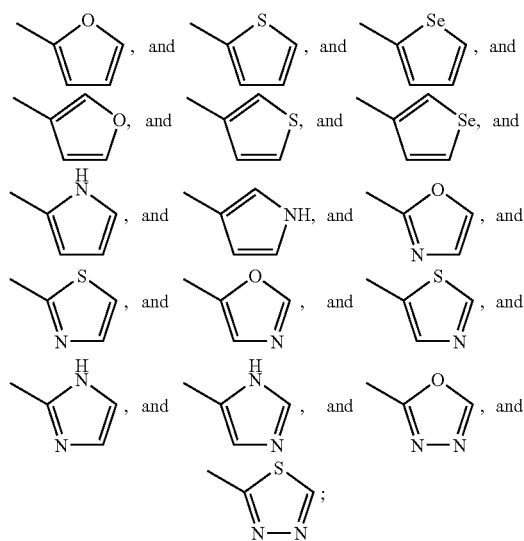

B represents a 6-membered aromatic monocyclic heterocyclic group selected from

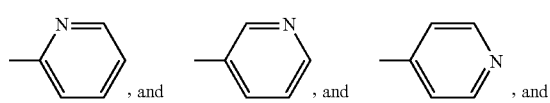

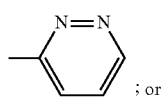

or

B represents an indol-2-yl, an indol-3-yl, an indol-5-yl or an indol-6-yl group;

which phenyl group, or 5–6-membered monocyclic heterocyclic groups, or indolyl groups may optionally be substituted one or more times with substituents selected from the group consisting of alkyl, alkoxy, halo, $CF_3$, $OCF_3$, CN and nitro; and a group for formula —NR"COR"', and —NR"SO$_2$R"', wherein R" and R"', independently of one another represents hydrogen, alkyl or phenyl; and a group of formula —CONR"R"' and —SO$_2$NR"R"', wherein R" and R"', independently of one another represents hydrogen, alkyl or phenyl, or wherein R" and R"', together with the N-atom to which they are bound, form a a piperidine, a piperazine or a morpholine ring.

In a yet more preferred embodiment

'A" represents a bivalent phenyl group of the formula

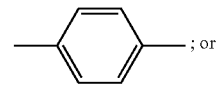

or

'A" represents a bivalent 6-membered aromatic monocyclic carbocyclic or heterocyclic group selected from

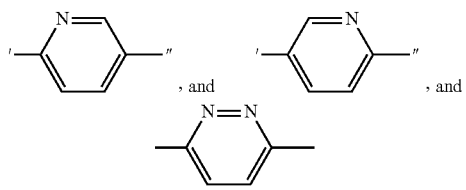

(read in the direction stated); and

B represents a phenyl group; or

B represents a 5-membered aromatic monocyclic heterocyclic group selected from

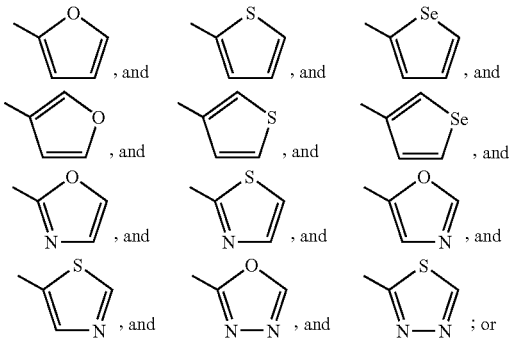

B represents a 6-membered aromatic monocyclic heterocyclic group selected from

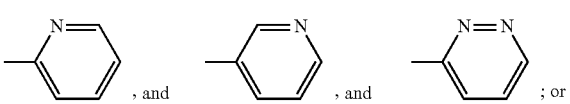

B represents an indol-2-yl, an indol-3-yl, an indol-5-yl or an indol-6-yl group.

In a still more preferred embodiment
'A" represents a bivalent phenyl group of the formula

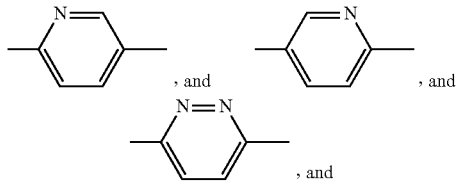

B represents a 5-membered aromatic monocyclic heterocyclic group selected from

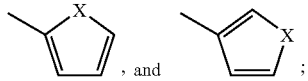

wherein X represents O, S or Se; and R' represents hydrogen or alkyl;

which 5-membered aromatic monocyclic heterocyclic group is optionally substituted substituted one or more times with substituents selected from the group consisting of alkyl, alkoxy, halogen, CF$_3$, CN and nitro.

In a most preferred embodiment the diazabicyclic biaryl derivative of the invention is 4-(6-Thien-3-yl-pyridazin-3-yl)-1,4-diazabicyclo[3.2.2]nonane;

4-(6-Pyridin-3-yl-pyridazin-3-yl)-1,4-diazabicyclo[3.2.2]nonane;

4-(6-Selenophen-3-yl-pyridazin-3-yl)-1,4-diazabicyclo[3.2.2]nonane;

4-Biphenyl-4-yl-1,4-diazabicyclo[3.2.2]nonane;

4-(6-Furan-2-yl-pyridazin-3-yl)-1,4-diazabicyclo[3.2.2]nonane;

4-(6-Thien-2-yl-pyridazin-3-yl)-1,4-diazabicyclo[3.2.2]nonane;

4-(6-Furan-3-yl-pyridazin-3-yl)-1,4-diazabicyclo[3.2.2]nonane;

4-(6-Thiazol-2-yl-pyridazin-3-yl)-1,4-diazabicyclo[3.2.2]nonane;

4-(6-Selenophen-2-yl-pyridazin-3-yl)-1,4-diazabicyclo[3.2.2]nonane;

4-(6-Indol-2-yl-pyridazin-3-yl)-1,4-diazabicyclo[3.2.2]nonane;

4-(6-Indol-3-yl-pyridazin-3-yl)-1,4-diazabicyclo[3.2.2]nonane;

4-(6-Indol-5-yl-pyridazin-3-yl)-1,4-diazabicyclo[3.2.2]nonane;

4-(6-Indol-6-yl-pyridazin-3-yl)-1,4-diazabicyclo[3.2.2]nonane;

4-(6-oxazol-2-yl-pyridazin-3-yl)-1,4-diazabicyclo[3.2.2]nonane;

4-(6-oxazol-5-yl-pyridazin-3-yl)-1,4-diazabicyclo[3.2.2]nonane;

4-(6-thiazol-5-yl-pyridazin-3-yl)-1,4-diazabicyclo[3.2.2]nonane;

4-[6-(1,3,4)-thiadiazol-2-yl-pyridazin-3-yl]-1,4-diazabicyclo[3.2.2]nonane; or

4-[6-(1,3,4)-oxadiazol-2-yl-pyridazin-3-yl]-1,4-diazabicyclo[3.2.2]nonane;

or an enantiomer or a mixture of its enantiomers, or a pharmaceutically acceptable salt thereof.

In a fifth preferred embodiment the diazabicyclic biaryl derivative of the invention is a compound of Formula I or Formula II wherein 'A" represents a bivalent 5-membered aromatic monocyclic heterocyclic group selected from

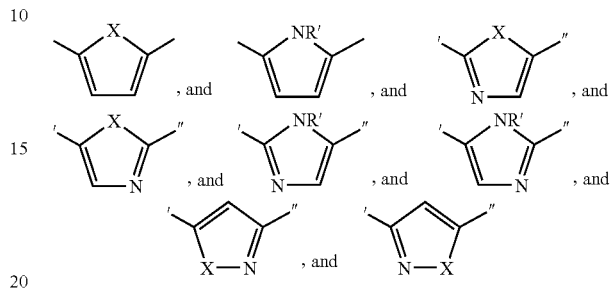

(read in the direction represented by ' and ");

wherein X represents O, S or Se; and R' represents hydrogen or alkyl; and

B represents a 5–6 membered aromatic monocyclic heterocyclic group; or

B represents an aromatic bicyclic heterocyclic group;

which monocyclic or bicyclic heterocyclic groups may optionally be substituted one or more times with substituents selected from the group consisting of alkyl, cycloalkyl, cycloalkyl-alkyl, alkoxy, cyanoalkyl, halo, CF$_3$, OCF$_3$, CN, amino and nitro; and a group for formula —NR"COR'", —NR"SO$_2$R'", wherein R" and R'", independently of one another represents hydrogen, alkyl, cycloalkyl, cycloalkyl-alkyl or phenyl; and a group of formula —CONR"R'" and —SO$_2$NR"R'", wherein R" and R'", independently of one another represents hydrogen, alkyl, cycloalkyl, cycloalkyl-alkyl or phenyl, or wherein R" and R'", together with the N-atom to which they are bound, form a heterocyclic ring.

In a more preferred embodiment

'A" represents a bivalent 5-membered aromatic monocyclic heterocyclic group selected from

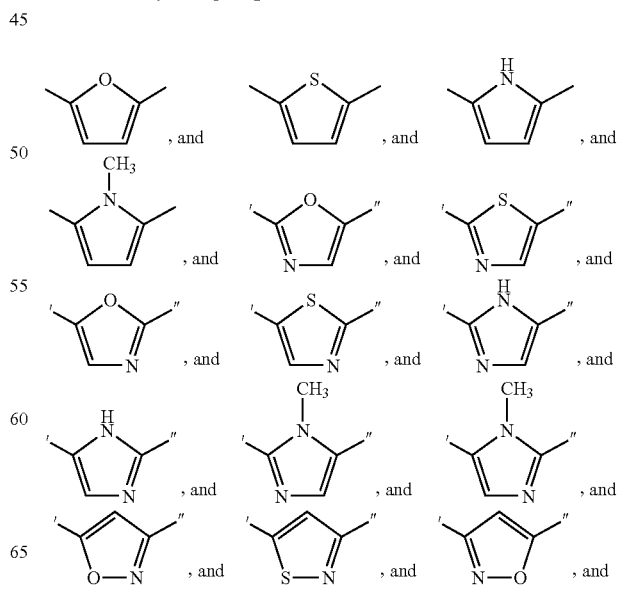

-continued

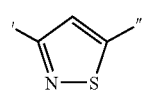

(read in the direction stated); and

B represents a 5-membered aromatic monocyclic heterocyclic group selected from

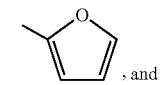 , and 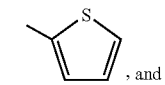 , and 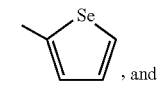 , and

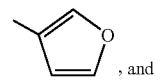 , and 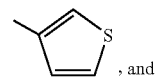 , and 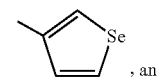 , and

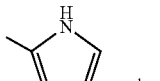 , and 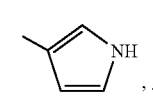 , and 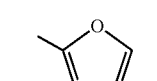 , and

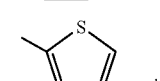 , and 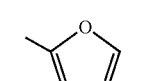 , and 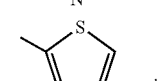 , and

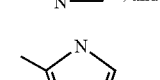 , and 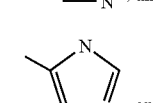 , and 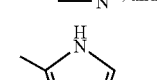 , and

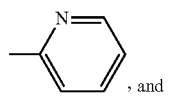 ; or

B represents a 6-membered aromatic monocyclic heterocyclic group selected from

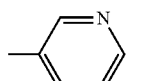 , and 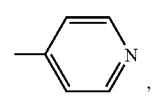 , and 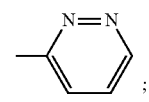 ;

which 5- or 6-membered aromatic monocyclic heterocyclic group is optionally substituted one or two times with substituents selected from the group consisting of alkyl, alkoxy halo, CF$_3$, OCF$_3$, CN and nitro; and a group for formula —NR"COR'", and —NR"SO$_2$R'", wherein R" and R'", independently of one another represents hydrogen, alkyl or phenyl; and a group of formula —CONR"R'" and —SO$_2$NR"R'", wherein R" and R'", independently of one another represents hydrogen, alkyl or phenyl, or wherein R" and R'", together with the N-atom to which they are bound, form a piperidine, a piperazine, a morpholine or a thiomorpholine ring.

In an even more preferred embodiment

'A" represents a bivalent 5-membered aromatic monocyclic heterocyclic group selected from

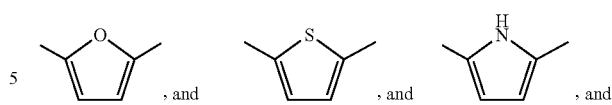

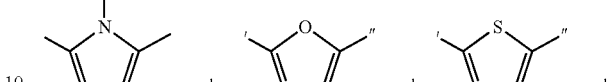

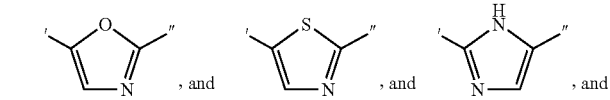

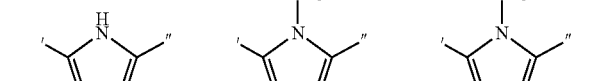

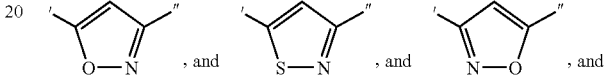

(read in the direction stated); and

B represents a 5-membered aromatic monocyclic heterocyclic group selected from

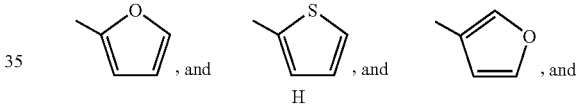

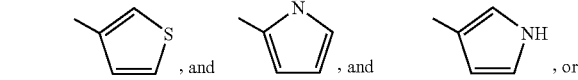

B represents a 6-membered aromatic monocyclic heterocyclic group selected from

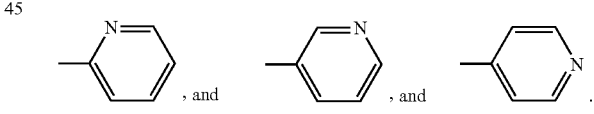

In a most preferred embodiment the diazabicyclic biaryl derivative of the invention is 4-(5-Thien-2-yl-pyrrol-2-yl)-1,4-diazabicyclo[3.2.2]nonane;

4-(5-Thien-2-yl-N-methyl-pyrrol-2-yl)-1,4-diazabicyclo[3.2.2]nonane;

4-(5-Thien-2-yl-thiazol-2-yl)-1,4-diazabicyclo[3.2.2]nonane;

4-(2-Thien-2-yl-thiazol-5-yl)-1,4-diazabicyclo[3.2.2]nonane;

4-(5-Thien-2-yl-furan-2-yl)-1,4-diazabicyclo[3.2.2]nonane;

4-(5-Thien-2-yl-thien-2-yl)-1,4-diazabicyclo[3.2.2]nonane;

4-(5-Thien-2-yl-imidazol-2-yl)-1,4-diazabicyclo[3.2.2]nonane;

4-(5-Thien-2-yl-N-methyl-imidazol-2-yl)-1,4-diazabicyclo[3.2.2]nonane;

4-(2-Thien-2-yl-imidazol-5-yl)-1,4-diazabicyclo[3.2.2]nonane;

4-(2-Thien-2-yl-N-methyl-imidazol-5-yl)-1,4-diazabicyclo[3.2.2]nonane;

4-(5-Thien-2-yl-oxazol-2-yl)-1,4-diazabicyclo[3.2.2]nonane;

4-(2-Thien-2-yl-oxazol-5-yl)-1,4-diazabicyclo[3.2.2]nonane;

4-(5-Thien-2-yl-isoxazol-3-yl)-1,4-diazabicyclo[3.2.2]nonane;

4-(5-Thien-2-yl-isothiazol-3-yl)-1,4-diazabicyclo[3.2.2]nonane;

4-(3-Thien-2-yl-isoxazol-5-yl)-1,4-diazabicyclo[3.2.2]nonane; or 4-(3-Thien-2-yl-isothiazol-5-yl)-1,4-diazabicyclo[3.2.2]nonane;

or an enantiomer or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention a 5–6 membered aromatic monocyclic heterocyclic designates a 5–6 membered heteroaryl, which holds one or more heteroatoms in its ring structure. Preferred heteroatoms include nitrogen (N), oxygen (O), and sulphur (S).

Preferred 5–6 membered heteroaryl groups of the invention include furanyl, in particular 2- or 3-furanyl; thienyl, in particular 2 or 3-thienyl; selenophenyl, in particular 2- or 3-selenophenyl; pyrrolyl (azolyl), in particular 2 or 3-pyrrolyl; oxazolyl, in particular oxazol-2,4 or 5-yl; thiazolyl, in particular thiazol-2,4 or 5-yl; imidazolyl, in particular 2 or 4-imidazolyl; pyrazolyl, in particular 3 or 4-pyrazolyl; isoxazolyl, in particular isoxazol-3,4 or 5-yl; isothiazolyl, in particular isothiazol-3,4 or 5-yl; oxadiazolyl, in particular 1,2,3-oxadiazol-4 or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4 or 5-yl, or 1,3,4-thiadiazol-2-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; and triazinyl, in particular 1,2,4- or 1,3,5-triazinyl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five- and six-membered heterocyclic rings containing one or more heteroatoms. Preferred heteroatoms include nitrogen (N), oxygen (O), and sulphur (S).

Preferred bicyclic heteroaryl groups of the invention include indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2,5 or 6-benzofuranyl; benzo[b]thienyl, in particular 2,5 or 6-benzothienyl; benzoimidazolyl, in particular 2,5 or 6-benzoimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; and pteridinyl, in particular 2,6 or 7-pteridinyl.

Pharmaceutically Acceptable Salts

The diazabicyclic biaryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Particularly preferred onium salts of the invention include those created at the N' position according to the following formula I'

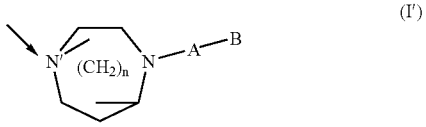

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Biaryl Derivatives

The diazabicyclic biaryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention relates to novel diazabicyclic biaryl derivatives, which are found to be cholinergic ligands at the nicotinic acetylcholine receptors (nAChR), and modulators of the monoamine receptors, in particular the biogenic amine transporters such as the serotonin receptor (5-HTR), the dopamine receptor (DAR) and the norepinephrine receptor (NER), and of the biogenic amine transporters for serotonin (5-HT), dopamine (DA) and norepinephrine (NE). Also preferred diazabicyclic biaryl derivatives of the invention show selective α7 activity.

In the context of this invention the term "modulator" covers agonists, partial agonists, antagonists and allosteric modulators of the receptor.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis, and diarrhoea.

In still another preferred embodiment the compounds of the invention may be useful for the treatment of mild, moderate or even severe pain of acute, chronic or recurrent character, as well as pain caused by migraine, postoperative pain, and phantom limb pain.

Finally the compounds of the invention may be useful for the treatment of withdrawal symptoms caused by termination of use of addictive substances. Such addictive substances include nicotine-containing products such as tobacco, opioids such as heroin, cocaine and morphine, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of the diazabicyclic biaryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic biaryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic biaryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of a diazabicyclic biaryl derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to bout 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane (Intermediate Compound)

Was prepared according to *J. Med. Chem.* 1993 36 2311–2320 and the following slightly modified method.

To a solution of 1,4-diazabicyclo[3.2.2]nonan-3-one (15.8 g, 113 mmol) in absolute dioxane (130 ml), LiAlH$_4$ (4.9 g, 130 mmol) was added under argon. The mixture was refluxed for 6 hours and then allowed to reach room temperatre. To this reaction mixture, water (5 ml in 10 ml of dioxane) was added, by drops, the mixture was stirred for 0.5 hour and then filtered off via glass filter. The solvent was evaporated and the residue was distilled using a Kugelrohr apparatus at 90° C. (0.1 mbar) to yield 1,4-diazabicyclo [3.2.2]nonane (11.1 g, 78%) as colourless hygroscopic material.

1,4-Diazabicyclo[3.2.2]nonan-3-one (Intermediate Compound)

To a solution of 3-quinuclidinone hydrochloride (45 g, 278 mmol) in 90 ml of water, hydroxylamine hydrochloride (21 g, 302 mmol) and sodium acetate ($CH_3COOH \times 3H_2O$, 83 g, 610 mmol) were added, and the mixture was stirred at 70° C. for 1 hour, and then cooled to 0° C. The separated crystalline material was filtered off (without washing) and dried in vacuo to yield 40.0 g of oxime.

The 3-quinuclidinone oxime (40.0 g) was added by small portions during 2 hours to polyphosphoric acid* (190 g), preheated to 120° C. During the reaction the temperature of the solution was kept at 130° C. After addition of all the oxime, the solution was stirred for 20 minutes at the same temperature, then transferred to an enamelled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated, and the solid residue dried up in vacuo to yield 30.0 g (77%) of a mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp 211–212° C.

The filtrate was evaporated and the residue was chromatographed on a silica gel column (Merck, 9385, 230–400 mesh) with acetone as eluent. The solvent was evaporated and the residue recrystallised from ethyl etanoate to yield 1,3-diazabicyclo[3.2.2]nonan-4-one (10.2 g, 26%) as colourless fine crystals with mp 125–126° C.

Polyphosphoric Acid*

85% Orthophosphoric acid (500 g, 294 ml, 4.337 mol) was placed into a 2000 ml flask and phosphor pentoxide (750 g, 5.284 mol) was added at room temperature (ratio acid-pentoxide, 2:3). The mixture was stirred at 200–220° C. for 2 hours to yield of 1250 g of polyphosphoric acid, containing 80% of $P_2O_5$.

3-Bromo-6-thien-3-yl-pyridazine (Intermediate Compound)

A mixture of 3,6-dibromo-pyridazine (8.45 g, 35.5 mmol), palladacycle (0.66 g, 0.71 mmol), palladium acetate (0.16 g, 0.71 mmol), tri-tert-butylphosphine (0.35 ml, 1.42 mmol), aqueous potassium carbonate (2 M, 107 mmol), 1,3-propanediol (7.7 ml, 107 mmol) and 1,4-dioxane (100 ml) was stirred at reflux for 1 hour. 3-Thienyl boronic acid (5.0 g, 39.0 mmol) was added and the mixture was stirred at reflux for 7 days. Aqueous sodium hydroxide (50 ml, 1M) was added and the mixture was extracted with ethyl acetate (2×100 ml). Chromatography on silica gel with ethyl acetate:petroleum (1:3) as solvent gave the title compound. Yield 1.5 g (18%).

3-Chloro-6-thien-3-yl-pyridazine hydrochloric acid salt (Intermediate Compound)

A mixture of 3-bromo-6-thien-3-yl-pyridazine (1.39 g, 5.8 mmol) and conc. hydrochloric acid (25 ml) was stirred at reflux for 4.5 hours. The reaction mixture was evaporated and the product was isolated in quantitative yield (1.35 g, 5.8 mmol).

4-(6-Bromo-pyridazin-3-yl)-1,4-diazabicyclo[3.2.2] nonane fumaric acid salt (Intermediate Compound)

A mixture of 3,6-dibromo-pyridazine (3.77 g, 15.85 mmol) 1,4-diazabicyclo[3.2.2]nonane (2.00 g, 15.85 mmol) and aqueous sodium hydroxide (10 ml, 4M) was stirred at 100° C. for 30 minutes. The mixture was extracted with dichloromethane (3×20 ml). Chromatography on silica gel with dichloromethane, 10% methanol and 1% aqueous ammonia as solvent gave the title compound as an oil. Yield 0.88 g, 20%.

4-[6-Thien-3-yl-pyridazin-3-yl]-1,4-diazabicyclo [3.2.2]nonane fumaric acid salt (Compound 1)

A mixture of 1,4-diazabicyclo[3.2.2]nonane (0.54 g, 4.29 mmol), 3-chloro-6-thien-3-yl-pyridazine hydrochloric acid salt (1.00 g, 4.29 mmol), triethylamine (3.00 ml, 21.4 mmol) and dioxane (15 ml) was stirred at reflux for 40 hours. Aqueous sodium hydroxide (1 M, 25 ml) was added and the mixture was extracted twice with ethyl acetate (2×20 ml). Chromatography on silica gel with dichloromethane, 10% methanol and 1% aqueous ammonia as solvent gave the title compound as an oil. The corresponding salt was obtained by addition of a diethyl ether and methanol mixture (9:1) saturated with fumaric acid. Yield 0.11 g, 9%. Mp 153.7° C.

Method A 4-(6-Pyridin-3-yl-pyridazin-3-yl)-1,4-diazabicyclo [3.2.2]nonane fumaric acid salt (Compound 2)

A mixture of 4-(6-bromo-pyridazin-3-yl)-1,4-diazabicyclo[3.2.2]nonane (0.49 g, 1.7 mmol), diethyl-3-pyridylborane (0.38 g, 2.6 mmol), aqueous potassium carbonate (2.6 ml, 2M), palladium(0)tetrakistriphenylphosphine (59 mg, 0.051 mmol), 1,3-propandiol (0.37 ml, 5.1 mmol) and dioxane (5 ml) was stirred at reflux for 15 hours. The mixture was evaporated. Aqueous sodium hydroxide (10 ml, 4M) was added. The mixture was extracted with dichloromethane (3×20 ml). Chromatography on silica gel with dichloromethane, 10% methanol and 1% aqueous ammonia as solvent gave the title compound as an oil. Yield 0.10 g, 21%.

The corresponding salt was obtained by addition of a diethyl ether and methanol mixture (9:1) saturated with fumaric acid. Mp 170.2–171.6° C.

Method B 4-(6-Selenophen-3-yl-pyridazin-3-yl)-1,4-diazabicyclo[3.2.2]nonane fumaric acid salt (Compound 3)

A mixture of 4-(6-bromo-pyridazin-3-yl)-1,4-diazabicyclo[3.2.2]nonane (1.1 g, 3.9 mmol), 3-trimethylstannylselenophene (2.3 g, 7.8 mmol), $PdCl_2(PPh_3)_2$ (82 mg, 0.11 mmol) and DMF (1 ml) was stirred at 100° C. for 15 hours. Aqueous sodium hydroxide (10 ml, 4M) was added. The mixture was extracted with dichloromethane (3×20 ml).

Chromatography on silica gel with dichloromethane, 10% methanol and 1% aqueous ammonia as solvent gave the title compound as an oil. Yield 0.14 g, 11%.

The corresponding salt was obtained by addition of a diethyl ether and methanol mixture (9:1) saturated with fumaric acid. Mp 181.2–182.2° C.

4-(6-Thien-2-yl-pyridazin-3-yl)-1,4-diazabicyclo[3.2.2]nonane fumaric acid salt (Compound 4)

Was prepared according to Method B from 2-trimetylstannylthiophene. Mp 185.5–187.4° C.

4-(6-Selenophen-2-yl-pyridazin-3-yl)-1,4-diazabicyclo[3.2.2]nonane fumaric acid salt (Compound 5)

Was prepared according to Method B from 2-trimetylstannylselenophene. Mp 194.7–195.9° C.

4-(6-Furan-2-yl-pyridazin-3-yl)-1,4-diazabicyclo[3.2.2]nonane fumaric acid salt (Compound 6)

Was prepared according to Method B from 2-trimetylstannylfuran. Mp 155.7–156.1° C.

4-(6-Furan-3-yl-pyridazin-3-yl)-1,4-diazabicyclo[3.2.2]nonane fumaric acid salt (Compound 7)

Was prepared according to Method B from 3-trimetylstannylfuran. Mp 116.9–119.0° C.

4-(6-Thiazol-2-yl-pyridazin-3-yl)-1,4-diazabicyclo[3.2.2]nonane fumaric acid salt (Compound 8)

Was prepared according to Method B from 2-thiazolylzinc chloride. Mp 175.2–179.2° C.

In analogy herewith the following compounds are prepared:

4-(5-Thien-2-yl-pyrrol-2-yl)-1,4-diazabicyclo[3.2.2]nonane fumaric acid salt (Compound 9);
4-(5-Thien-2-yl-N-methyl-pyrrol-2-yl)-1,4-diazabicyclo[3.2.2]nonane fumaric acid salt (Compound 10);
4-(5-Thien-2-yl-thiazol-2-yl)-1,4-diazabicyclo[3.2.2]nonane fumaric acid salt (Compound 11);
4-(2-Thien-2-yl-thiazol-5-yl)-1,4-diazabicyclo[3.2.2]nonane fumaric acid salt (Compound 12);
4-(5-Thien-2-yl-furan-2-yl)-1,4-diazabicyclo[3.2.2]nonane fumaric acid salt (Compound 13);
4-(5-Thien-2-yl-thien-2-yl)-1,4-diazabicyclo[3.2.2]nonane fumaric acid salt (Compound 14);
4-(5-Thien-2-yl-imidazol-2-yl)-1,4-diazabicyclo[3.2.2]nonane fumaric acid salt (Compound 15);
4-(5-Thien-2-yl-N-methyl-imidazol-2-yl)-1,4-diazabicyclo[3.2.2]nonane fumaric acid salt (Compound 16);
4-(2-Thien-2-yl-imidazol-5-yl)-1,4-diazabicyclo[3.2.2]nonane fumaric acid salt (Compound 17);
4-(2-Thien-2-yl-N-methyl-imidazol-5-yl)-1,4-diazabicyclo[3.2.2]nonane fumaric acid salt (Compound 18);
4-(5-Thien-2-yl-oxazol-2-yl)-1,4-diazabicyclo[3.2.2]nonane fumaric acid salt (Compound 19);
4-(2-Thien-2-yl-oxazol-5-yl)-1,4-diazabicyclo[3.2.2]nonane fumaric acid salt (Compound 20);
4-(5-Thien-2-yl-isoxazol-3-yl)-1,4-diazabicyclo[3.2.2]nonane fumaric acid salt (Compound 21);
4-(5-Thien-2-yl-isothiazol-3-yl)-1,4-diazabicyclo[3.2.2]nonane fumaric acid salt (Compound 22);
4-(3-Thien-2-yl-isoxazol-5-yl)-1,4-diazabicyclo[3.2.2]nonane fumaric acid salt (Compound 23);
4-(3-Thien-2-yl-isothiazol-5-yl)-1,4-diazabicyclo[3.2.2]nonane fumaric acid salt (Compound 24);
4-(6-Indol-2-yl-pyridazin-3-yl)-1,4-diazabicyclo[3.2.2]nonane fumaric acid salt (Compound 25);
4-(6-Indol-3-yl-pyridazin-3-yl)-1,4-diazabicyclo[3.2.2]nonane fumaric acid salt (Compound 26);
4-(6-Indol-5-yl-pyridazin-3-yl)-1,4-diazabicyclo[3.2.2]nonane fumaric acid salt (Compound 27);
4-(6-Indol-6-yl-pyridazin-3-yl)-1,4-diazabicyclo[3.2.2]nonane fumaric acid salt (Compound 28);
4-(6-oxazol-2-yl-pyridazin-3-yl)-1,4-diazabicyclo[3.2.2]nonane fumaric acid salt (Compound 29);
4-(6-oxazol-5-yl-pyridazin-3-yl)-1,4-diazabicyclo[3.2.2]nonane fumaric acid salt (Compound 30);
4-(6-thiazol-5-yl-pyridazin-3-yl)-1,4-diazabicyclo[3.2.2]nonane fumaric acid salt (Compound 31);
4-[6-(1,3,4)-thiadiazol-2-yl-pyridazin-3-yl]-1,4-diazabicyclo[3.2.2]nonane fumaric acid salt (Compound 32); and
4-[6-(1,3,4)-oxadiazol-2-yl-pyridazin-3-yl]-1,4-diazabicyclo[3.2.2]nonane fumaric acid salt (Compound 33).

4-Biphenyl-4-yl-1,4-diazabicyclo[3.2.2]nonane fumaric acid salt (Compound 34)

A mixture of 1,4-diazabicyclo[3.2.2]nonane (1.0 g, 7.9 mmol), 4-bromobiphenyl (1.85 g, 7.9 mmol), potassium tert-butoxide (1.85 g, 15.8 mmol), Pd(0)(PPh$_3$)$_4$ (0.27 g, 0.24 mmol) and dioxane (10 ml) was stirred at 100° C. for 15 hours. The mixture was evaporated. Aqueous sodium hydroxide (10 ml, 4M) was added. The mixture was extracted with dichloromethane (3×20 ml). Chromatography on silica gel with dichloromethane, 10% methanol and 1% aqueous ammonia as solvent gave the title compound as an oil. Yield 65 mg, 3%.

The corresponding salt was obtained by addition of a diethyl ether and methanol mixture (9:1) saturated with fumaric acid. Mp 196.3–196.9° C.

Example 2

In Vitro Inhibition of $^3$H-α-Bungarotoxine Binding in Rat Brain

In this example the affinity of the compounds of the invention for binding to α$_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist.

$^3$H-α-Bungarotoxine labels nicotinic acetylcholine receptors formed by the α$_7$ subunit isoform found in brain and the α$_1$ isoform in the neuromuscular junction.

Tissue Preparation

Preparations are performed at 0–4° C. Cerebral cortices from male Wistar rats (150–250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C. Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{50}$ (the concentration of the test substance which inhibits the specific binding of $^3$H-α-bungarotoxin by 50%).

The results of these experiments are presented in Table 1 below.

TABLE 1

Inhibition of $^3$H-α-Bungarotoxine Binding

| Compound No. | IC$_{50}$ (μM) |
|---|---|
| 1 | 0.038 |
| 4 | 0.044 |
| 5 | 0.0065 |
| 7 | 0.022 |
| 34 | 0.024 |

The invention claimed is:

1. A diazabicyclic biaryl compound represented by Formula I

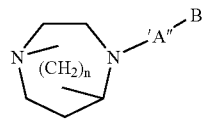

(I)

any of its enantiomers or any mixture of its enantiomers, or a pharmaceutically acceptable salt thereof, wherein
n is 1, 2 or 3; and
'A" represents a bivalent phenyl group of the formula

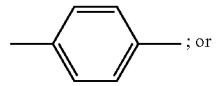

'A" represents a bivalent 6-membered aromatic monocyclic carbocyclic or heterocyclic group selected from

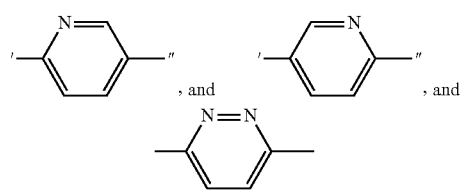

(read in the direction represented by ' and "); and
B represents a phenyl group; or B represents a 5-membered aromatic monocyclic heterocyclic group selected from

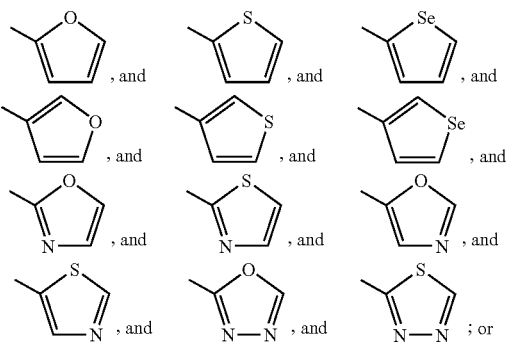

B represents a 6-membered aromatic monocyclic heterocyclic group selected from

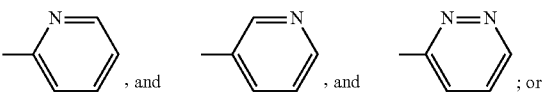

B represents an indol-2-yl, an indol-3-yl, and indol-5-yl, or an indol-6-yl group.

2. The diazabicyclic biaryl compound of claim 1, which is 4-(6-Thien-3-yl-pyridazin-3-yl)-1,4-diazabicyclo[3.2.2]nonane;
4-(6-Pyridin-3-yl-pyridazin-3-yl)-1,4-diazabicyclo[3.2.2]nonane;
4-(6-Selenophen-3-yl-pyridazin-3-yl)-1,4-diazabicyclo[3.2.2]nonane;
4-(6Furan-2-yl-pyridazin-3-yl)-1,4-diazabicyclo[3.2.2]nonane;
4-(6-Thien-2-yl-pyridazin-3-yl)-1,4-diazabicyelo[3.2.2]nonane;
4-(6-Furan-3-yl-pyridazin-3-yl)-1,4-diazabicyclo[3.2.2]nonane;
4-(6Thiazol-2-yl-pyridazin-3-yl)-1,4-diazabicyclo[3.2.2]nonane;
4-(6-Selenophen-2-yl-pyridazin-3-yl)-1,4-diazabicyclo[3.2.2]nonane;
4-(6-Indol-2-yl-pyridazin-3-yl)-1,4-diazabicyclo[3.2.2]nonane;
4-(6-Indol-3-yl-pyridazin-3-yl)-1,4-diazabicyclo[3.2.2]nonane;
4-(6-Indol-5-yl-pyridazin-3-yl)-1,4-diazabicyclo[3.2.2]nonane;
4-(6-Indol-6-yl-pyridazin-3-yl)-1,4-diazabicyclo[3.2.2]nonane;
4-(6-oxazol-2-yl-pyridazin-3-yl)-1,4-diazabicyclo[3.2.2]nonane;
4-(6-oxazol-5-yl-pyridazin-3-yl)-1,4-diazabicyclo[3.2.2]nonane;
4-(6thiazol-5-yl-pyridazin-3-yl)-1,4-diazabicio[3.2.2]nonane;
4-[(6-(1,3,4)-thiadiazol-2-yl]-pyridazin-3-yl-1,4-diazabicyclo[3.2.2]nonane; or 4-[6-(1,3,4)-oxadiazol-2-yl]-pyridazin-3-yl-1,4-diaza-bieyelo[3.2.2]nonane;

or an enantiomer or a mixture of its enantiomers, or a pharmaceutically acceptable salt thereof.

3. A pharmaceutical composition comprising a therapeutically effective amount of a diazabicyclic biaryl compound of claim 1, or a pharmaceutically-acceptable addition salt thereof, together with at least one pharmaceutically-acceptable carrier or diluent.

4. A method of treatment of a disease or a disorder or a condition of a living animal body, including a human, wherein the disease, disorder or condition is responsive to modulation of cholinergic receptors and/or monoamine receptors and wherein the disease, disorder, or condition is selected from the group consisting of Alzheimer's disease and Parkinson's disease, which method comprises the step of administering to a living animal body in need thereof a therapeutically effective amount of a diazabicyclic biaryl compound of claim 1.

* * * * *